(12) United States Patent
Ventura et al.

(10) Patent No.: US 9,555,119 B2
(45) Date of Patent: Jan. 31, 2017

(54) COMPOSITION AND METHOD FOR DELIVERY OF HYDROPHOBIC ACTIVE AGENTS

(71) Applicant: SurModics, Inc., Eden Prairie, MN (US)

(72) Inventors: Joseph Ventura, Elk Grove, CA (US); Shannon Wadman, Minneapolis, MN (US); Joram Slager, St. Louis Park, MN (US); Joseph Schmidt McGonigle, Minneapolis, MN (US); Robert W. Hergenrother, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 14/072,520

(22) Filed: Nov. 5, 2013

(65) Prior Publication Data

US 2014/0142166 A1    May 22, 2014

Related U.S. Application Data

(60) Provisional application No. 61/722,735, filed on Nov. 5, 2012, provisional application No. 61/740,713, filed on Dec. 21, 2012.

(51) Int. Cl.
| | |
|---|---|
| *A61K 31/337* | (2006.01) |
| *A61K 47/34* | (2006.01) |
| *A61L 27/18* | (2006.01) |
| *A61L 27/54* | (2006.01) |
| *A61K 9/00* | (2006.01) |

(52) U.S. Cl.
CPC .............. *A61K 47/34* (2013.01); *A61K 31/337* (2013.01); *A61L 27/18* (2013.01); *A61L 27/54* (2013.01); *A61K 9/0019* (2013.01); *A61L 2300/416* (2013.01); *A61L 2300/63* (2013.01); *A61L 2400/06* (2013.01)

(58) Field of Classification Search
CPC .................................................. A61K 31/337
See application file for complete search history.

(56) References Cited

U.S. PATENT DOCUMENTS

| | | | |
|---|---|---|---|
| 3,389,099 A | 6/1968 | Dressler et al. | |
| 3,936,391 A | 2/1976 | Gabby et al. | |
| 4,456,627 A | 6/1984 | Van Heteren | |
| 4,490,421 A | 12/1984 | Levy | |
| 4,638,045 A | 1/1987 | Kohn et al. | |
| 5,002,582 A | 3/1991 | Guire et al. | |
| 5,073,641 A | 12/1991 | Bundgaard et al. | |
| 5,102,402 A | 4/1992 | Dror et al. | |
| 5,201,753 A | 4/1993 | Lampropoulos et al. | |
| 5,297,607 A | 3/1994 | Beauchamp | |
| 5,304,121 A | 4/1994 | Sahatjian | |
| 5,397,307 A | 3/1995 | Goodin | |
| 5,414,075 A | 5/1995 | Swan et al. | |
| 5,466,719 A | 11/1995 | Jakobson et al. | |
| 5,502,219 A | 3/1996 | Harris | |
| 5,556,383 A | 9/1996 | Wang et al. | |
| 5,558,642 A | 9/1996 | Schweich, Jr. et al. | |
| 5,585,506 A | 12/1996 | Harvey | |
| 5,616,608 A | 4/1997 | Kinsella et al. | |
| 5,637,460 A | 6/1997 | Swan et al. | |
| 5,714,360 A | 2/1998 | Swan et al. | |
| 5,728,732 A | 3/1998 | Corey | |
| 5,811,447 A | 9/1998 | Kunz et al. | |
| 5,833,657 A | 11/1998 | Reinhardt et al. | |
| 5,858,653 A | 1/1999 | Duran et al. | |
| 5,891,451 A | 4/1999 | Guerrero et al. | |
| 5,980,948 A | 11/1999 | Goedemoed et al. | |
| 6,007,833 A | 12/1999 | Chudzik et al. | |
| 6,077,698 A | 6/2000 | Swan et al. | |
| 6,168,748 B1 | 1/2001 | Wang et al. | |
| 6,210,364 B1 | 4/2001 | Anderson et al. | |
| 6,278,018 B1 | 8/2001 | Swan | |
| 6,299,604 B1 | 10/2001 | Ragheb et al. | |

(Continued)

FOREIGN PATENT DOCUMENTS

| | | |
|---|---|---|
| CN | 103906505 | 7/2014 |
| EP | 1430917 | 6/2004 |

(Continued)

OTHER PUBLICATIONS

Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative," Pharmaceutical Research, vol. 12, No. 3, 1995 1995, 397-405.

Babayan, V K. "Preparation and Properties of Some Polyglycerol Esters of Short and Medium Length Fatty Acids," Journal of the American Oil Chemists' Society Jul. 1971 Jul. 1971, 307-309.

Babayan, V K. et al., "Nutritional Studies of Polyglycerol Esters," The Journal of the American Oil Chemist' Society vol. 41, Jun. 1964 Jun. 1964, 434-438.

Birnbaum, Duane T. et al., "Microparticle Drug Delivery Systems," Chapter 6, Drug Delivery Systems in Cancer Therapy, 2003, (pp. 117-135).

Bodansky, M et al., "Utilization of Polyglycerol Esters," Biochemistry vol. 32 Aug. 30, 1938, 1938-1942.

(Continued)

*Primary Examiner* — Zohreh Fay
(74) *Attorney, Agent, or Firm* — Pauly, DeVries Smith & Deffner, L.L.C.

(57) ABSTRACT

Disclosed herein is a delivery composition for administering a hydrophobic active agent. In one embodiment, a delivery composition for local administration of a hydrophobic active agent to a tissue or organ of a patient is disclosed. In one embodiment, the delivery composition includes a cationic delivery agent, a therapeutically effective amount of a hydrophobic active agent and a pharmaceutically acceptable aqueous carrier. In one embodiment, the cationic delivery agent includes polyethyleneimine (PEI). In a more specific embodiment, the cationic delivery agent includes branched PEI. Methods of making the delivery composition, as well as kits and methods of use are also disclosed.

17 Claims, 6 Drawing Sheets

(56) References Cited

U.S. PATENT DOCUMENTS

| | | |
|---|---|---|
| 6,328,710 B1 | 12/2001 | Wang et al. |
| 6,340,465 B1 | 1/2002 | Hsu et al. |
| 6,444,324 B1 | 9/2002 | Sjoquist et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,514,734 B1 | 2/2003 | Clapper et al. |
| 6,515,009 B1 | 2/2003 | Kunz et al. |
| 6,544,544 B2 | 4/2003 | Hunter et al. |
| 6,603,040 B1 | 8/2003 | Swan |
| 6,620,904 B2 | 9/2003 | Lemke |
| 6,623,452 B2 | 9/2003 | Chien et al. |
| 6,663,662 B2 | 12/2003 | Pacetti et al. |
| 6,703,040 B2 | 3/2004 | Katsarava et al. |
| 6,730,064 B2 | 5/2004 | Ragheb et al. |
| 6,762,019 B2 | 7/2004 | Swan et al. |
| 7,034,765 B2 | 4/2006 | Fischer et al. |
| 7,138,541 B2 | 11/2006 | Swan |
| 7,309,593 B2 | 12/2007 | Ofstead et al. |
| 7,438,710 B2 | 10/2008 | Anderson et al. |
| 7,507,469 B2 | 3/2009 | Yao et al. |
| 7,696,259 B2 | 4/2010 | Hanley et al. |
| 7,731,685 B2 | 6/2010 | Schaeffer et al. |
| 7,736,689 B2 | 6/2010 | Chappa et al. |
| 7,758,892 B1 | 7/2010 | Chen et al. |
| 7,797,033 B2 | 9/2010 | D'andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,039,524 B2 | 10/2011 | Chappa et al. |
| 8,172,793 B2 | 5/2012 | Choules et al. |
| 8,202,530 B2 | 6/2012 | Hossainy et al. |
| 8,246,576 B2 | 8/2012 | Slager |
| 8,257,305 B2 | 9/2012 | Scheller et al. |
| 8,293,262 B2 | 10/2012 | Chen et al. |
| 8,439,868 B2 | 5/2013 | Scheller et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao et al. |
| 8,673,387 B2 | 3/2014 | Bates et al. |
| 8,697,112 B2 | 4/2014 | DeTizio et al. |
| 8,809,411 B2 | 8/2014 | Rooijmans |
| 8,871,819 B2 | 10/2014 | Meyering et al. |
| 8,889,760 B2 | 11/2014 | Kurdyumov et al. |
| 2002/0006493 A1 | 1/2002 | Chabrecek et al. |
| 2002/0123801 A1 | 9/2002 | Pacetti et al. |
| 2003/0065355 A1 | 4/2003 | Weber |
| 2003/0195611 A1 | 10/2003 | Greenhalgh et al. |
| 2003/0211135 A1 | 11/2003 | Greenhalgh et al. |
| 2004/0051201 A1 | 3/2004 | Greenhalgh et al. |
| 2004/0105839 A1* | 6/2004 | Park .................. 424/78.17 |
| 2005/0100580 A1 | 5/2005 | Osborne et al. |
| 2005/0187605 A1 | 8/2005 | Greenhalgh et al. |
| 2005/0255142 A1 | 11/2005 | Chudzik et al. |
| 2006/0018948 A1 | 1/2006 | Guire et al. |
| 2006/0200232 A1 | 9/2006 | Phaneuf et al. |
| 2006/0240194 A1 | 10/2006 | Lemke et al. |
| 2007/0026037 A1 | 2/2007 | Kloke et al. |
| 2007/0048351 A1 | 3/2007 | Lunn |
| 2007/0065481 A1 | 3/2007 | Chudzik et al. |
| 2007/0154591 A1 | 7/2007 | Andersen |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0220054 A1 | 9/2008 | Shastri et al. |
| 2008/0233183 A1* | 9/2008 | McCook et al. .......... 424/450 |
| 2009/0030504 A1 | 1/2009 | Weber et al. |
| 2009/0043276 A1 | 2/2009 | Weber et al. |
| 2009/0081276 A1 | 3/2009 | Alsberg et al. |
| 2009/0226501 A1 | 9/2009 | Parsonage et al. |
| 2009/0227946 A1 | 9/2009 | Kangas et al. |
| 2010/0015240 A1 | 1/2010 | Biggs |
| 2010/0076377 A1 | 3/2010 | Ehrenreich et al. |
| 2010/0076401 A1 | 3/2010 | Von et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0292668 A1 | 11/2010 | Slager |
| 2011/0022027 A1 | 1/2011 | Morishita et al. |
| 2011/0144373 A1 | 6/2011 | Swan et al. |
| 2011/0245367 A1 | 10/2011 | Kurdyumov et al. |
| 2011/0250255 A1 | 10/2011 | Parsonage et al. |
| 2011/0275725 A1 | 11/2011 | Meyering et al. |
| 2012/0039983 A1 | 2/2012 | Uhrich et al. |
| 2012/0046384 A2 | 2/2012 | Kurdyumov et al. |
| 2012/0083734 A1 | 4/2012 | Ayres et al. |
| 2012/0148852 A1 | 6/2012 | Jelle et al. |
| 2012/0177742 A1 | 7/2012 | Mcclain et al. |
| 2012/0177910 A1 | 7/2012 | Weber et al. |
| 2012/0296274 A1 | 11/2012 | Slager |
| 2013/0143056 A1 | 6/2013 | Swan et al. |
| 2013/0190689 A1 | 7/2013 | Slager |
| 2013/0302529 A1 | 11/2013 | Kurdyumov |
| 2014/0162083 A1 | 6/2014 | Kurdyumov et al. |
| 2014/0336571 A1 | 11/2014 | Slager |
| 2015/0140107 A1 | 5/2015 | Slager et al. |
| 2015/0283092 A1 | 10/2015 | Ruddy et al. |

FOREIGN PATENT DOCUMENTS

| | | |
|---|---|---|
| EP | 1994950 | 11/2008 |
| EP | 1997525 | 12/2008 |
| EP | 2251050 | 11/2010 |
| EP | 2098230 | 6/2012 |
| EP | 2292225 | 6/2012 |
| EP | 2569023 | 3/2013 |
| JP | 2003506417 | 2/2003 |
| JP | 2007537005 | 12/2007 |
| JP | 2008519771 | 6/2008 |
| JP | 2009523493 | 6/2009 |
| JP | 2014515348 | 6/2014 |
| JP | 5945534 | 6/2016 |
| WO | 0110468 | 2/2001 |
| WO | 2005079754 | 9/2005 |
| WO | 2005113034 | 12/2005 |
| WO | 2006019848 | 2/2006 |
| WO | 2006026187 | 3/2006 |
| WO | 2006053175 | 5/2006 |
| WO | 2009051614 | 4/2009 |
| WO | 2009113605 | 9/2009 |
| WO | 2009121629 | 10/2009 |
| WO | 2010111517 | 9/2010 |
| WO | 2010129328 | 11/2010 |
| WO | 2011052089 | 5/2011 |
| WO | 2011143237 A1 | 11/2011 |
| WO | 2012162061 | 11/2012 |
| WO | 2014071387 | 5/2014 |
| WO | 2014186729 | 11/2014 |

OTHER PUBLICATIONS

Charlemagne, D et al., "Enzymatic Synthesis of Polyglycerol-Fatty Acid Esters in a Solvent-Free System," Journal for American Oil Chemists' Society vol. 72. No. 1 (1995) 1995, 61-65.

"Communication Pursuant to Article 94(3) EPC," for European Patent Application No. 11720694.6, mailed Oct. 25, 2013 (6 pages).

"Communication Pursuant to Rules 161(1) and 162 EPC," for European Patent Application No. 12723063.9, mailed Jan. 21, 2014 (2 pages).

De Meulenaer, B et al., "Development of Chromatographic Method for the Determination of Degree of Polymerisation of Polyglycerols and Polyglycerol Fatty Acid Esters," Chromatographia vol. 51, No. 1/2, Jan. 2000 Jan. 2000, 44-52.

Dobson, Kevin S. et al., "The Preparation of Polyglycerol Esters Suitable as Low-Caloric Fat Substitutes," Journal of the American Oil Chemists' Society vol. 70, No. 11 (Nov. 1993) Nov. 1993, 1089-1092.

Dow Corning Corp., "A guide to Silane Solutions," 2005.

(56) References Cited

OTHER PUBLICATIONS

Fao Nutrition Meetings Report, "Toxicological Evaluation of Some Antimicrobials, Antioxidants, Emulsifiers, Stabilizers, Flour-treatment Agents, Acids and Bases," FAO Nutrition Meetings Report Series No. 40A, B, C WHO/Food Add. 67.29 1966, 1-4.
File History for Related U.S. Appl. No. 13/104,383 downloaded May 11, 2015, 204 pages.
File History for Related Application U.S. Appl. No. 13/469,844 downloaded May 11, 2015, 239 pages.
File History for Related Application U.S. Appl. No. 13/793,390 downloaded May 11, 2015, 134 pages.
File History for Related Application U.S. Appl. No. 14/280,170 downloaded May 11, 2015, 124 pages.
File History for Related Application U.S. Appl. No. 14/609,270 downloaded May 11, 2015, 137 pages.
Finkel, Toren "Relief with Rapamycin: mTOR Inhibition Protects Against Radiation-Induced Mucositis," Cell Stem Cell, vol. 11:3, Sep. 7, 2012 (4 pages).
"First Office Action," for Chinese Patent Application No. 2012800328049, mailed Mar. 2, 2015 (7 pages) including English translation.
From Wikipedia, "Electrospinning," From Wikipedia, the free encyclopedia, http://en.wikipedia.org/wiki/Electrospinning, downloaded Sep. 13, 2010; last updated Sep. 2, 2010, 2009, (pp. 1-6).
Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29) Oct. 30, 2009.
Hagemeier, C J. "Ocular Tolerability of Poly(lactide-co-glyoliide) Microspheres Following Subconjunctival and Inravitreal Injection in Rabbit Eyes," ARVO 2010 Presented ARVO 2010, Hall B/C, May 6, 2010 8:30am-10:15am May 6, 2010.
Howes, D et al., "The Fate of Ingested Glyceran Esters of Condensed Castor Oil Fatty Acids [Polyglycerol Polyricinoleate (PGPR)] in the Rat," Food and Chemical Toxicology 36 (1998) 719-738 1998, 719-738.
"International Preliminary Report on Patentability," for PCT/US2011/035951, mailed Nov. 22, 2012 (8 pages).
"International Preliminary Report on Patentability," for PCT/US2012/038158, mailed Nov. 28, 2013 (8 pages).
"International Search Report and Written Opinion," for PCT/US2012/035951, mailed Aug. 3, 2011 (12 pages).
"International Search Report and Written Opinion," for PCT/US2012/038158, mailed Sep. 27, 2012 (13 pages).
"International Search Report and Written Opinion," for PCT/US2013/068539, mailed Jan. 22, 2014 (12 pages).
"International Search Report and Written Opinion," for PCT/US2014/038435, mailed Aug. 25, 2014 (13 pages).
Kallinteri, Paraskevi et al., "Novel Functionalized Biodegradable Polymers for Nanoparticle Drug Delivery Systems," Biomacromolecules 2005 2006, 6, 1885-1894; American Chemical Society Apr. 27, 2005, 1885-1894.
Kumar, Majeti N.V. R. "Nano and Microparticles as Controlled Drug Delivery Devices," J. Pharm Pharmaceut Sci, 3(2), 2000 (pp. 234-258).
Liu, Rong "Water-Insoluble Drug Formulation," CRC Press, 2nd Ed., 2008 (pp. 1-3).
Love, Kevin T. et al., "Lipid-like materials for low-dose, in vivo gene silencing," www.pnas.org/cgi/doi/10.1073/pnas.0910603106 (6 pages).
Mcintyre, R T. "Polyglycerol esters," Journal of American Oil Chemists' Society Nov. 1979 (vol. 56) Nov. 1979, 835A-840A.
Orafei, Hossein et al., "Novel Poly(glycerol-adipate) Polymers Used for Nanoparticle Making: A Study of Surface Free Energy," Iranian Journal of Pharmaceutical Research (2008), 7 (1): 11-19 2008, 11-19.
Puri, Sanyogita "Drug Incorporation and Release of Water Soluble Drugs from Novel Functionalized Poly(glycerol adipate) Nanoparticles," Journal of Controlled Release 125 (2008) 59-67 Oct. 10, 2007, 59-67.

Renkin, Eugene M. "Filtration, Diffusion, and Molecular Sieving Through Porous Cellulose Membranes," Nov. 20, 1954 (pp. 1-19).
"Response to Communication Pursuant to Rule 161 and 162 EPC," for European Patent Application 12723063.9, mailed Jan. 21, 2014 and filed with the EPO Jul. 18, 2014 (4 pages).
Salamone, Joseph "Hydrophic Polymers (for Friction Reduction)," Polymeric Materials Encyclopedia, vol. 12 (1996) p. 3107.
Santoyo, Antonio B. et al., "Biosynthesis of Polyglycerol Polyricinoleate (PGPR) with Rhizopus Arrhizus Lipase," Journal of Biotechnology 131S (2007) S74-S97 2007, S82.
Solvay Chemicals, "Polyglycerols for Ester Production," PGLC-05-002 Revised Aug. 2008 CGR4004, From www.solvaychemicals.us Aug. 2008, 1-7.
Takatori, Toshihito "Design of Controlled-Release Morphine Suppositories Containing Polyglycerol Ester of Fatty Acid," Biological Phamacy Bulletin 28(8) 1480-1484 (2005), vol. 28, No. 8 Aug. 2005, 1480-1484.
Yamagata, Yutaka et al., "Novel Sustained Release Dosage Forms of Proteins Using Polyglycerol Esters of Fatty Acids," Journal of Controlled Release vol. 63, Issue 3 Feb. 3, 2000, 319-329.
"Communication Under Rule 71(3) EPC," for European Patent Application No. 11720694.6, mailed on Jun. 1, 2015 (6 pages).
"International Preliminary Report on Patentability," for PCT/US2013/068539, mailed May 14, 2015 (9 pages).
"Non-Final Office Action," for Japanese Patent Application No. 2013-510249, mailed on Jun. 2, 2015 (6 pages) with English Summary.
"Response to Non-Final Office Action," for U.S. Appl. No. 13/793,390, mailed Feb. 5, 2015 and filed with the USPTO Jul. 6, 2015 (11 pages).
"Response to Non-Final Office Action," for U.S. Appl. No. 14/609,270, mailed Mar. 27, 2015 and filed with the USPTO Jun. 25, 2015 (9 pages).
Avella, "Addition of glycerol plasticizer to seaweeds derived alginates: Influences of microstructure on chemical-physical properties," Carbohydrate Polymers vol. 69, Issue 3, Jun. 25, 2007, pp. 503-511.
"Final Office Action," for U.S. Appl. No. 13/793,390, mailed on Feb. 12, 2016 (8 pages).
"Invitation to Pay Additional Fees and Partial Search Report," for PCT Application No. PCT/US2016/015644, mailed May 3, 2016 (8 pages).
"Non-Final Office Action," for U.S. Appl. No. 14/280,170, mailed Feb. 12, 2016 (51 pages).
"Office Action," for Japanese Patent Application No. 2014511494 mailed Feb. 5, 2016 (13 pages) with English Translation.
"Response to Communication Pursuant to Rules 161(1) and 162 EPC," for European Application No. 13792207.6, filed with the EPO Feb. 3, 2016 (4 pages).
"Response to Final Office Action," for U.S. Appl. No. 14/609,270, mailed Dec. 8, 2015 and filed with the USPTO Apr. 1, 2016 (12 pages).
"Response to Non-Final Office Action," for U.S. Appl. No. 13/469,844, mailed Dec. 3, 2015 and filed with the USPTO Mar. 30, 2016 (9 pages).
"Communication Pursuant to Rules 161(1) and 162 EPC," for European Application No. 13792207.6, mailed Aug. 5, 2015 (2 pages).
"Communication Pursuant to Rules 161(1) and 162 EPC," for European Patent Application No. 14730381.2, mailed Jan. 15, 2016 (2 pages).
"Final Office Action," for U.S. Appl. No. 13/793,390 mailed Nov. 16, 2015 (16 pages).
"Final Office Action," for U.S. Appl. No. 14/609,270 mailed Dec. 8, 2015 (27 pages).
"International Preliminary Report on Patentability," for PCT/US2014/038435 mailed Nov. 26, 2015 (10 pages).
"Non-Final Office Action," for U.S. Appl. No. 13/469,844 mailed Dec. 3, 2015 (19 pages).
"Response to Final Office Action," for U.S. Appl. No. 13/793,390, mailed Nov. 16, 2015 and filed with the USPTO Jan. 19, 2016 (17 pages).

(56) References Cited

OTHER PUBLICATIONS

"International Search Report & Written Opinion," for PCT/US2016/015644 mailed Jul. 11, 2016 (17 pages).
"Response to Non-Final Office Action," for U.S. Appl. No. 14/280,170, mailed Feb. 12, 2016 and filed with the USPTO Jul. 12, 2016 (18 pages).
"Final Office Action," for U.S. Appl. No. 14/280,170 mailed Oct. 21, 2016 (40 pages).

\* cited by examiner

COMPOSITION AND METHOD FOR DELIVERY OF HYDROPHOBIC ACTIVE AGENTS

This application claims the benefit of U.S. Provisional Application No. 61/722,735, filed Nov. 5, 2012 and U.S. Provisional Application No. 61/740,713, filed Dec. 21, 2012, the contents of which are herein incorporated by reference.

FIELD OF THE INVENTION

The present invention relates to compositions and methods for delivering biologically active agents to a patient. More specifically, the present invention relates to compositions and methods for local administration of hydrophobic active agents to a patient.

BACKGROUND OF THE INVENTION

Generally, the initial focus during development of a biologically active agent is the physiochemical properties of the pharmaceutical compound, in particular the therapeutic function of the compound. Once the biological activity of the active agent is defined, the design focus typically shifts to the systems and formulations by which the active agent is delivered. In particular, one focus during development of delivery systems and formulations is the provision of a system or formulation in which therapeutic titers of the active agent are able to reach the appropriate anatomical location or compartment after administration.

The phrase "route of administration" refers to the path by which an active agent is brought into contact with the body and is determined primarily by the properties of the active agent and by the therapeutic objectives. The route of administration that is chosen for a particular active agent may have a profound effect upon the speed and efficiency of the active agent upon administration.

In general, routes of administration can be classified by whether the effect is local or systemic. For local delivery, an active agent is applied directly to the tissue or organ for which treatment is sought. The effect of local delivery is limited primarily to the tissue or organ to which the active agent is applied. For example, local delivery may be accomplished through the use of compositions such as liniments, lotions, drops, ointments, creams, suppositories, emulsions, solutions, suspensions and the like. Local delivery can also be accomplished using special delivery devices such as catheters, syringes or implantables designed to convey drug to a specific region in the body. In contrast, an active agent administered systemically enters the blood or lymphatic supply and may be felt some distance from the site of administration. For systemic delivery, oral and parenteral routes are typically used.

However, there is still a need in the art for simple, inexpensive delivery systems which are easily prepared and which can deliver a broad range of active agents to their intended targets, especially in the case of hydrophobic active agents.

SUMMARY OF THE INVENTION

Disclosed herein is a delivery composition for administration of a hydrophobic active agent, along with kits that include the delivery compositions, methods of making the delivery composition, and methods of using the delivery composition. In particular the invention provides a delivery composition for local administration of a hydrophobic active agent.

In one embodiment, the delivery composition includes a cationic delivery agent, a therapeutically effective amount of the hydrophobic active agent; and a pharmaceutically acceptable aqueous carrier. In one embodiment, the hydrophobic active agent is combined with the pharmaceutically acceptable aqueous carrier to form a suspension. In another embodiment, the cationic delivery agent is dissolved in the pharmaceutically acceptable carrier to form a solution. In a more particular embodiment, the cationic delivery agent includes polyetheyleneimine (PEI), for example, dissolved PEI, more particularly, branched PEI. In one embodiment, the cationic delivery agent includes branched PEI with a molecular weight of at least about 25 kD and up to about 5000 kD, at least about 70 kD and up to about 4000 kD, at least about 100 kD and up to about 3000 kD, or at least about 500 kD and up to about 1000 kD. In one embodiment, the branched PEI has a ratio of primary:secondary:tertiary amines between about 1:3:1 and about 1:1:1, or between about 1:2:1 and about 1:1:1. In one embodiment, the delivery composition includes cationic delivery agent:hydrophobic active agent at a ratio of at least about 1:1 and up to about 1:25, at least about 1:2 and up to about 1:20, or at least about 1:5 and up to about 1:10. In another embodiment, the delivery composition includes at least about 0.05 mg/ml, 0.1 mg/ml, 0.5 mg/ml or 1 mg/ml and up to about 25 mg/ml cationic delivery agent and at least about 5 mg/ml and up to about 125 mg/ml hydrophobic active agent. In another embodiment, the aqueous carrier includes water. In another embodiment, the delivery composition has a pH between 5 and 9, 6 and 8, or 7 and 8. In one embodiment, the hydrophobic active agent is an antiproliferative, analgesic, anti-inflammatory, anti-arrhythmic, anti-bacterial, anti-coagulant, anti-hypertensive, anti-muscarinic, anti-neoplastic, beta-blocker, cardiac inotropic agent, corticosteroids, lipid regulating agents, anti-anginal agents, or combinations thereof. In a more particular embodiment, the hydrophobic active agent is an antiproliferative selected from paclitaxel, sirolimus (rapamycin), everolimus, biolimus A9, zotarolimus, tacrolimus, and pimecrolimus and mixtures thereof.

The invention also provides a method of making the delivery compositions. In one embodiment, the method includes combining the hydrophobic active agent with a pharmaceutically acceptable aqueous carrier to form an active agent suspension; and adding the cationic delivery agent to the active agent suspension to form the delivery composition. In one embodiment, the method includes a step of crystallizing the hydrophobic active agent before combining the hydrophobic active agent with the aqueous carrier to form the active agent suspension. In another embodiment, the method includes a step of combining the cationic delivery agent with an aqueous solution to form a cationic delivery agent solution before adding the cationic delivery agent to the active agent suspension. In one embodiment, the pH of the cationic delivery agent solution is adjusted to a pH between 5 and 9 before adding the cationic delivery agent to the active agent suspension.

In another embodiment, the method of making the delivery composition includes combining the hydrophobic active agent with the cationic delivery agent to form an active agent mixture; and combining the active agent mixture with the aqueous carrier to form the delivery composition. In one embodiment, the method includes a step of crystallizing the active agent mixture before combining the mixture with the aqueous carrier.

The invention also provides kits that include a therapeutically effective amount of hydrophobic active agent; and cationic delivery agent. The kit components (i.e., the hydrophobic active agent and/or the cationic delivery agent) can be included in the kit as solids or as aqueous solutions, either individually or combined. The solid kit component can be either crystalline or amorphous.

The invention also provides methods for local administration of a therapeutically or prophylactically effective amount of a hydrophobic active agent to a tissue or organ of a patient.

BRIEF DESCRIPTION OF THE FIGURES

The invention may be more completely understood in connection with the following drawings, in which.

Figure 1:
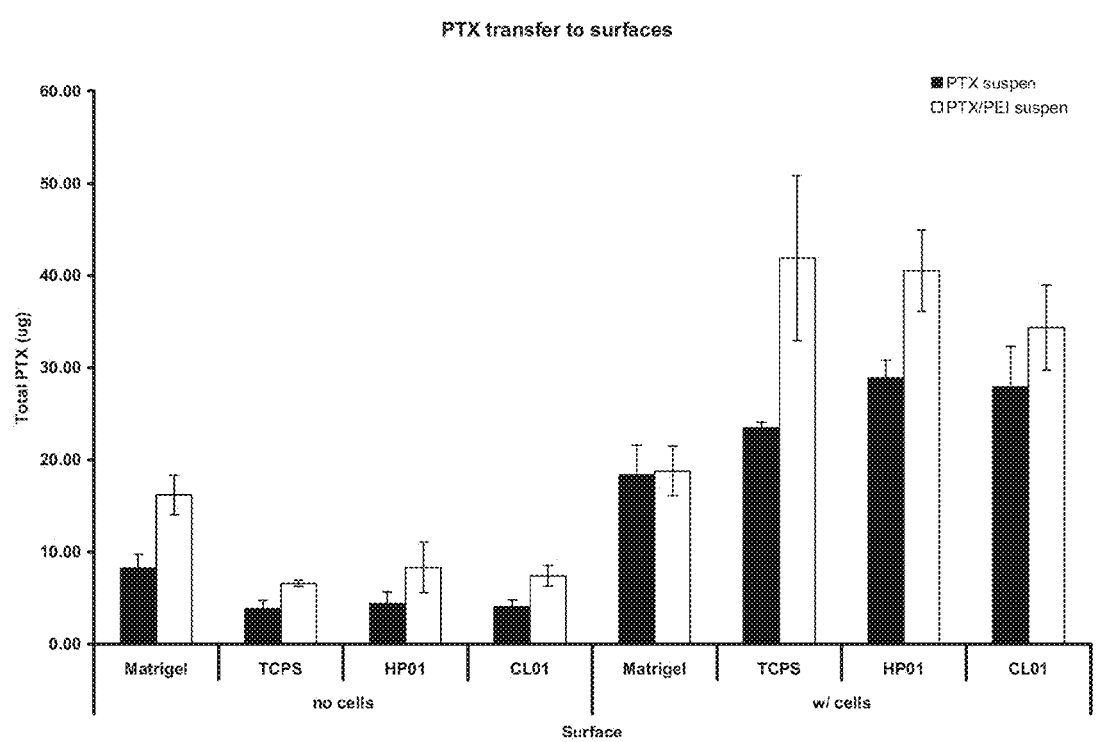
FIG. 1 is a graph showing the amount of paclitaxel adhered and/or transferred to different surfaces with or without seeded endothelial cells in the presence or absence of PEI.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention described herein provides compositions and methods for delivery of an active agent to a patient. The compositions are referred to herein as "delivery compositions." As used herein, the term "route of administration" refers to the path by which an active agent is brought into contact with the body. The particular route of administration used with a particular active agent is determined primarily by properties of the active agent and by therapeutic objectives. In one embodiment, the invention provides compositions and methods for local administration of an active agent to a patient. As used herein, the term "local administration" refers to a route of administration in which a therapeutically effective amount of an active agent is applied directly to the tissue or organ for which treatment is sought, wherein the therapeutic effect of the active agent is limited primarily to the tissue or organ to which the active agent is applied. One advantage of local administration of an active agent is the ability to attain a pharmaceutically relevant concentration of active agent at a desired site, while reducing the risk of systemic toxicity. It is noted that some active agent may disperse from the local site of administration during local delivery. In general, less than about 50%, 40%, 30%, 20%, 10%, 5%, 4%, 3%, 2% or 1% of the active agent disperses from the site of administration during local administration. In contrast, for systemic delivery, the active agent is administered at a convenient access site, for example, intravascularly, intramuscularly, or orally and travels through the blood stream to the tissues or organs for which treatment is sought. In systemic delivery, more than 50% of the active agent disperses from the site of administration during systemic administration.

In a more particular embodiment, the invention provides compositions and methods for local delivery of a therapeutic amount of a hydrophobic active agent to a tissue or organ of a patient. In one embodiment, the invention provides a composition for local delivery of a hydrophobic active agent, wherein the composition includes the hydrophobic active agent and a cationic delivery agent. Suitable cationic delivery agent delivery and hydrophobic therapeutic agents are described in greater detail below. In another embodiment, one or more additives may be included in the delivery composition. Exemplary additive components are described in greater detail below.

Hydrophobic Active Agents

In one embodiment, the delivery composition includes one or more hydrophobic active agents. In general, the term "hydrophobic active agent" refers to an active agent having solubility in water of less than about 100 µg/mL at 25° C. and neutral pH, less than about 10 µg/mL at 25° C. and neutral pH, or less than about 5 µg/ml at 25° C. and neutral pH. In one embodiment, the hydrophobic active agent is crystalline. In general, the term "crystalline" refers to a thermodynamically stable solid form of an active agent having "long range molecular order" in which the molecules are packed in a regularly ordered, repeating pattern. In another embodiment, the hydrophobic active agent is amorphous. The term "amorphous" refers to a solid form of an active agent in which the molecules do not have "long range molecular order", but rather are randomly arranged or retain only a "short range molecular order" typical of liquids. In general, crystalline forms of an active agent tend to have a higher level of purity and more stability than amorphous forms of the same active agent. Additionally, the crystalline form of an active agent tends to be more soluble than the amorphous form. One of skill in the art is aware of methods for determining whether an active agent is in a crystalline or amorphous form, for example, using x-ray diffraction.

The amount of hydrophobic active agent included in the delivery composition can vary depending upon many factors including the desired therapeutic outcome. However, the composition of the invention generally includes at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml or 150 mg/ml hydrophobic active agent.

It will be appreciated that hydrophobic active agents can include agents having many different types of activities. In some embodiments, hydrophobic active agents can include, but are not limited to, antiproliferatives such as paclitaxel, sirolimus (rapamycin), everolimus, biolimus A9, zotarolimus, tacrolimus, and pimecrolimus and mixtures thereof; analgesics and anti-inflammatory agents such as aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecamide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexyl HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as aminone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other hydrophobic active agents include, but are not limited to, active agents for treatment of hypertension (HTN), such as guanethidine.

In a particular embodiment, the hydrophobic active agent includes paclitaxel, sirolimus (rapamycin), everolimus, biolimus A9, zotarolimus, tacrolimus, and pimecrolimus and mixtures thereof.

In one embodiment, the hydrophobic active agent includes chemotherapeutics, exemplified by the family of fluorouracils (e.g. 4-FU and 5-FU) and Carmustine (bischloroethylnitrosourea: BCNU).

In one embodiment, the hydrophobic active agent is combined with a cationic delivery agent in solution. In another embodiment, solid hydrophobic active agent, amorphous or crystalline, is combined with pure or neat cationic delivery agent, amorphous or crystalline, to form a mixture.

In other embodiments, the hydrophobic active agents is conjugated to a cationic delivery agent. The conjugation can include a hydrophobic active agent covalently bonded to the cationic delivery agent. In some embodiments wherein the hydrophobic agent is conjugated to the cationic delivery agent a linking agent can be used to attach the hydrophobic agent to the cationic delivery agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

Cationic Delivery Agents

In one embodiment, the delivery composition includes a hydrophobic active agent and cationic delivery agent. While not wishing to be bound by theory, it is believed that the charge provided by the cationic delivery agents results in the composition being electrostatically attracted to negative charges and/or polar groups associated with the lipid bilayer present on or in a tissues or organs of a patient or charged/polar groups associated with the extracellular matrix (e.g, collagen, fibronectin, laminin, etc.). Consequently, combining an active agent, particularly a hydrophobic active agent with a cationic delivery agent in a composition for local administration helps retain the hydrophobic active agent near the site of administration. It is also thought that the cationic delivery agent may increase tissue permeability, thereby enhancing uptake of the active agent by the target tissue and/or organ.

In general, the upper limit for the amount of cationic delivery agent that is included in the delivery composition is guided by the toxicity limit for the given cationic delivery agent or the solubility of the cationic delivery agent in the aqueous carrier used in the composition. However, in one embodiment, the ratio of cationic delivery agent:hydrophobic active agent can be up to 1:1. The lower limit for the amount of cationic delivery agent that is included in the composition is guided by the efficacy of the composition. In general, the inventors have found that a ratio of cationic delivery agent:hydrophobic active agent of 1:50 has limited efficacy. Consequently, the composition generally has a ratio of cationic delivery agent:hydrophobic active agent of at least 1:25. In one embodiment, the ratio of cationic delivery agent:hydrophobic active agent is between about 1:1 and about 1:25. In another embodiment, the ratio of cationic delivery agent:hydrophobic active agent is at least about 1:2, 1:5 or 1:10 and up to about 1:10, 1:15, 1:20 or 1:25. In one embodiment, the composition of the invention includes at least about 0.1 mg/ml, 0.5 mg/ml, 1 mg/ml, 2 mg/ml, 3 mg/ml, 4 mg/ml, or 5 mg/ml and up to about 5 mg/ml, 10 mg/ml, 15 mg/ml, 20 mg/ml or 25 mg/ml cationic delivery agent.

Cationic delivery agents used in embodiments herein include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic delivery agents used in embodiments herein can include those having the general formula X-Y, wherein X is a positively charged group in aqueous solution at neutral pH and Y is a moiety exhibiting hydrophobic properties. In some embodiments, the cationic delivery agent can include a hydrophilic head and a hydrophobic tail, along with one or more positively charged groups, typically in the area of the hydrophilic head.

Cationic delivery agents can specifically include cationic lipids and net neutral lipids that have a cationic group. Exemplary lipids can include, but are not limited to, 3β-[N—(N',N'-dimethylaminoethane)-carbamoyl]cholesterol hydrochloride (DC-cholesterol); 1,2-dioleoyl-3-trimethyl-ammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethyl-ammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).

Cationic delivery agents can specifically include cationic polymers. Cationic delivery agents can also include polycation-containing cyclodextrin, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polypropylenimine, polyamidoamine dendrimers (PAMAM; available from Sigma Aldrich), cationic polyoxazoline and poly(beta-aminoesters). Cationic delivery agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

In one embodiment, the cationic delivery agent includes polyethyleneimine (PEI). PEI is a basic cationic aliphatic polymer which can be linear or branched. Linear PEI is a solid at room temperature and includes predominantly secondary amines. Branched PEIs are liquid at room temperature and include primary, secondary and tertiary amino groups. The ratio of primary:secondary:tertiary amino groups reflects the amount of branching, wherein the relative amount of secondary amino groups decreases as the amount of branching increases. In one embodiment, PEI includes primary:secondary:tertiary amino groups at a ratio of between about 1:3:1 and 1:1:1, or between about 1:2:1 and 1:1:1. In another embodiment, PEI includes primary:secondary:tertiary amino groups at a ratio of between about 1:2:1 and 1:1:1, 1:1.1:1, 1:1.2:1, 1:1.3:1, 1:1.4:1, 1:1.5:1, 1:1.6:1, 1:1.7:1, 1:1.8:1, or 1:1.9:1. In another embodiment, PEI is linear and includes predominantly secondary amines. In one embodiment, branched PEI includes no more than about 30%, 35%, 40%, 45%, 50%, 55%, 60%, 65%, 70%, or 75% secondary amine groups. In other embodiments, PEI includes one or more quaternary amine groups.

In one method, PEI is synthesized from monomers that include a three-membered ring in which two corners of the molecule have (—$CH_2$—) linkages and the third corner includes a secondary amine group (=NH). In the presence of a catalyst the three-membered ring is converted into a highly branched polymer with about 25% primary amine groups, 50% secondary amine groups, and 25% tertiary amine groups. The branched polymers can be copolymerized to produce PEI having a variety of molecular weights, from 2 kD up to 5000 kD. In one embodiment, PEI has a molecular weight of at least about 25 kD, 50 kD, 70 kD, 75 kD, 100 kD, 150 kD, 200 kD, 250 kD, 300 kD, 350 kD, 400 kD, 450 kD, 500 kD, 550 kD, 600 kD, 650 kD, 700 kD, 750 kD, 800 kD, 850 kD, 900 kD, 950 kD or 1000 kD and up to about 1000 kD, 1500 kD, 2000 kD, 2500 kD, 3000 kD, 3500 kD, 4000 kD, 4500 kD or 5000 kD. Methods for synthesizing linear PEI are also known.

The inventors have found that linear PEI is not as effective as a cationic delivery agent for hydrophobic active agents when compared to branched PEI. This could be because linear PEI is less soluble in aqueous carriers, such as water, than branched PEI. In general, linear PEI is only soluble in aqueous solutions such as water when it is heated to a temperature of at least about 50° C. Branched PEI is generally soluble in aqueous carriers such as water and a 5% aqueous solution of PEI typically has a pH between about 10 and 12. As the pH of a solution or suspension containing PEI is changed, the nature of the PEI molecule also changes. In particular, when the pH of a solution or suspension of PEI is between about 5 and about 9, the stability of the solution can be improved. The pH of a PEI solution can be adjusted by titrating with an acid, such as hydrochloric acid (HCl) having a concentration between about 1M and about 10 M. Advantageously, a solution with a pH between about 5 and about 9 is well suited for use in vivo. Branched PEI is highly soluble or miscible in water. The solubility limit for branched PEI depends on the amount of branching and molecular weight. In one embodiment, branched PEI has a solubility of at least about 0.01 mg/ml, 0.1 mg/ml, 1 mg/ml, 5 mg/ml, 10 mg/ml, 25 mg/ml or 50 mg/ml, and up to about 25 mg/ml, 50 mg/ml, 75 mg/ml, 100 mg/ml, 150 mg/ml or 200 mg/ml at room temperature (i.e., between about 20° C. and about 25° C.). Generally, PEI is used as a cationic delivery agent in an aqueous solution having a concentration of at least about 0.1 μg/ml, 0.2 μg/ml, 0.3 μg/ml, 0.4 μg/ml, 0.5 μg/ml, and up to about 0.6 μg/ml, 0.7 μg/ml, 0.8 μg/ml, 0.9 μg/ml or 1 μg/ml, wherein the aqueous solution is buffered to a pH of at least about 5, 6 or 7 or up to about 7, 8 or 9.

In other embodiments of the present disclosure, cationic delivery agents having a positive charge in aqueous solutions at neutral pH include the following Compounds (A-I):

Compound A

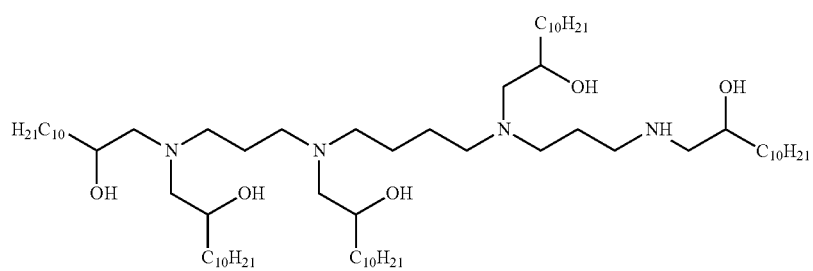

-continued
Compound B
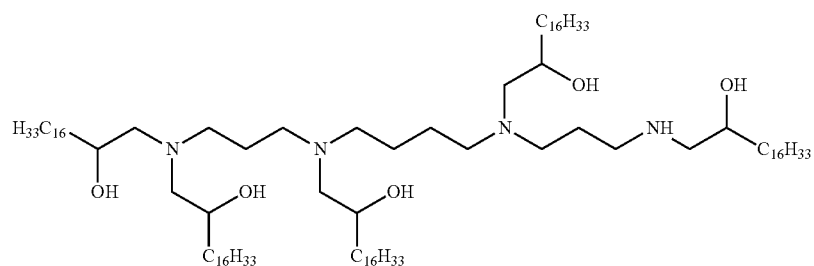
Compound C
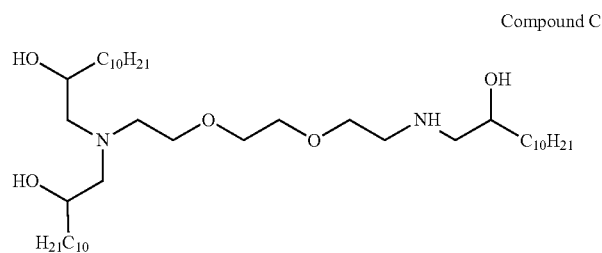
Compound D
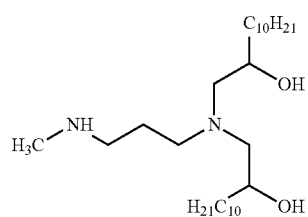
Compound E
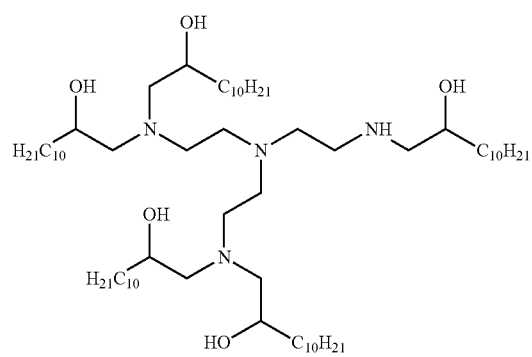
Compound F
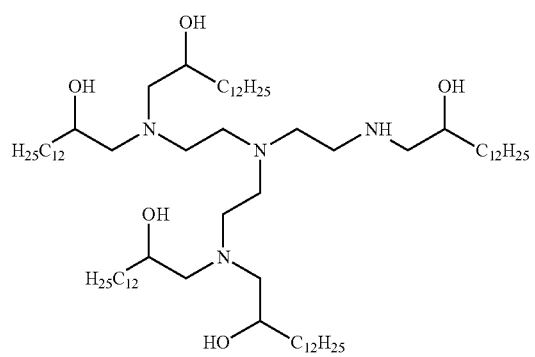
Compound G
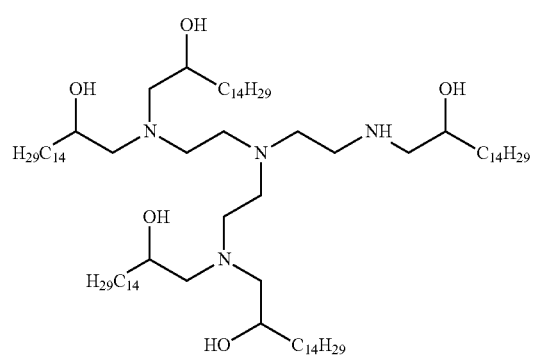
Compound H
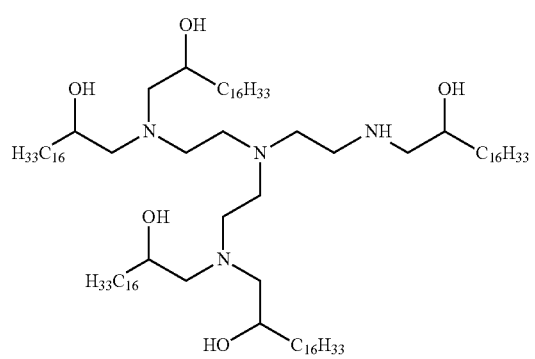
Compound I
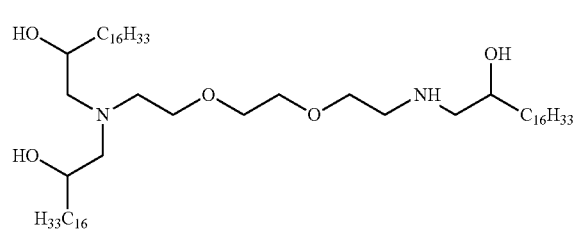

Additionally, other cationic delivery agents include structures of the general Formula I:

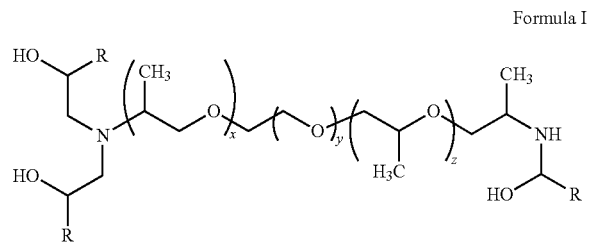

Formula I

TABLE 1

Values for Variables x + z,
y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Methods for making cationic delivery agents, such as those listed above, are described in more detail in U.S. patent application Ser. No. 13/469,844, entitled "DELIVERY OF COATED HYDROPHOBIC ACTIVE AGENT PARTICLES," the disclosure of which is hereby incorporated by reference herein in its entirety. In general, cationic delivery agents, such as those listed above, can generally be prepared by the reaction of an appropriate hydrophobic epoxide (e.g. oleyl epoxide) with a multi-functional amine (e.g. propylene diamine). Details of the synthesis of related cationic delivery agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic delivery agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic delivery agents can include moieties used to condense nucleic acids (for example lipids, peptides and other cationic polymers). In some instances these cationic delivery agents can be used to form lipoplexes and polyplexes.

Additional Components

In other embodiments, the delivery composition of the invention can include one or more additional components, such as a diluent, excipient, adjuvant, emulsifier, buffer, stabilizer, preservative, and the like. In one embodiment, the delivery composition includes one or more contrast agents, for example, an iodinated radiocontrast agent.

In another embodiment, the delivery composition of the invention can include one or more agents that enhance tissue penetration, including, but not limited to zonulin, propylene glycol, mono-, di- or tri-glycerides etc.

Exemplary additive components can further include compounds that stabilize poorly water soluble pharmaceutical agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

Other additives include saccharides. Saccharides can include monosaccharides, disaccharides, trisaccharides, oligosaccharides, and polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

Saccharides can also include derivatives of polysaccharides. It will be appreciated that polysaccharides include a variety of functional groups that can serve as attachment points or can otherwise be chemically modified in order to alter characteristics of the saccharide. As just one example, it will be appreciated that saccharide backbones generally include substantial numbers of hydroxyl groups that can be utilized to derivatize the saccharide. Saccharides can also include copolymers and/or terpolymers, and the like, that include saccharide and/or saccharide subunits and/or blocks.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (avg. molecular weight ~95,000 Da) and Glucidex™ 2 (avg. molecular weight ~300,000 Da) are available from Roquette (France); and MALTRIN™ maltodextrins of various molecular weights, including molecular weights from about 12,000 Da to 15,000 Da are available from GPC (Muscatine, Iowa). Examples of other hydrophobic polysaccharide derivatives are disclosed in US Patent Publication 2007/0260054 (Chudzik), which is incorporated herein by reference.

In another embodiment, the composition includes one or more amphiphilic additive. Amphiphilic compounds include those having a relatively hydrophobic portion and a relatively hydrophilic portion. Exemplary amphiphilic compounds can include, but are not limited to, polymers including, at least blocks of, polyvinylpyrrolidone, polyvinyl alcohol, polyethylene glycol, polyoxazolines (such as poly (2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLURONIC®. It will be appreciated that many aspects of the copolymer can be varied such the characteristics can be customized. One exemplary poloxamer is PLURONIC® F68 (nonionic, co-polymer of ethylene and propylene oxide commercially available from BASF Corporation; also designated as F68 and poloxamer F68), which refers to a poloxamer having a solid form at room temperature, a polyoxypropylene molecular mass of approximately 1,800 g/mol and roughly 80% polyoxyethylene content, with a total molecular weight of approximately 8,400 g/mol, the copolymer terminating in primary hydroxyl groups.

In yet other embodiments, additive components can further include additives that effectively reverse the effect of drug uptake in tissue. Exemplary components that induce this reversal effect include heparin and heparin derivatives. Other negatively charged additive components that can complex with the cationic delivery agent of the present disclosure can also provide this reversal effect.

Aqueous Carrier

In one embodiment, the delivery composition includes a hydrophobic active agent and a cationic delivery agent in a pharmaceutically acceptable aqueous carrier. As used herein, a "pharmaceutically acceptable carrier" refers to a carrier or diluent that does not cause significant irritation to an organism and does not abrogate the biological activity and properties of the administered composition. In one embodiment, the aqueous carrier includes water or buffered saline. In a more particular embodiment, the aqueous carrier includes deuterium-depleted water (DDW). In one embodiment, the hydrophobic active agent and/or the cationic delivery agent are suspended in water. In one embodiment, the carrier includes a minor amount (e.g., less than about 20%, 15%, 10%, 9%, 8%, 7%, 6%, 5%, 4%, 3%, 2% or 1%) of a biocompatible solvent. As used herein, the term "biocompatible solvent" refers to a solvent that is considered non-toxic and does not elicit an immunological response at the amounts included in the carrier. Examples of biocompatible solvents include, but are not limited to, ethanol, ethyl lactate, acetone, dimethylsulfoxide (DMSO), and combinations thereof. In one embodiment, the hydrophobic active agent is suspended in water as a coated therapeutic agent. In one embodiment, a mixing or agitation step can be performed in order to allow the hydrophobic active agent to interface with the cationic delivery agent. In some embodiments, the cationic delivery agent surrounds and/or encapsulates the particulate hydrophobic active agent to form a coated active agent particle.

In one embodiment, the pH of the composition is adjusted to at least about 5, 6 or 7 and up to about 7, 8 or 9.

Method of Making

In one embodiment, the invention is directed towards methods of making the delivery compositions described herein. In one embodiment, the delivery composition includes a hydrophobic active agent and a cationic delivery agent in an aqueous carrier. In a more particular embodiment, the cationic delivery agent includes PEI. In another embodiment, the cationic delivery agent includes branched PEI. In a specific embodiment, the hydrophobic active agent is paclitaxel, sirolimus (rapamycin), everolimus, biolimus A9, zotarolimus, tacrolimus, and pimecrolimus and mixtures thereof.

In some embodiments, the hydrophobic active agent can be processed, for example, by milling of the active agent. In some embodiments, processing of the hydrophobic active agent can include crystallization. In other embodiments, processing of the hydrophobic active agent can include lyophilizing of the active agent.

In one embodiment, the hydrophobic active agent is suspended in an aqueous carrier such as water. By combining the hydrophobic active agent and a cationic delivery agent, coated active agent particles can be formed. By way of example, a cationic agent, in water or other aqueous solvent, can be added to a hydrophobic active agent suspension. In some embodiments, a mixing or agitation step can be performed in order to allow the hydrophobic active agent to interface with the cationic agent. In some embodiments, the cationic agent will surround or encapsulate the particulate hydrophobic active agent. In one embodiment, the hydrophobic active agent has a particle size of at least about 0.1 µm, 0.2 µm, 0.3 µm, 0.4 µm, 0.5 µm or 1 µm and less than about 10 µm, 5 µm, 4 µm, 3 µm, 2 µm or 1 µm.

In one embodiment, an active agent solution or suspension is first made by combining a hydrophobic active agent with an aqueous solvent to form an active agent solution or suspension. After the active agent solution or suspension is formed, the cationic delivery agent is added to form a delivery composition. In one embodiment, the hydrophobic active agent is crystallized before it is combined with the aqueous solvent to form the active agent solution or suspension. In another embodiment, the hydrophobic active agent is amorphous when it is combined with the aqueous solvent to form the active agent solution or suspension. In another embodiment, the cationic delivery agent is combined with an aqueous solvent to form a cationic delivery agent solution before the cationic delivery agent is combined with the active agent solution or suspension. In one embodiment, the pH of the cationic delivery agent solution is buffered to between about 5 and 9 before the cationic delivery agent is added to the active agent solution or suspension.

In another embodiment, the delivery composition is made by combining the hydrophobic active agent and the cationic delivery agent to form an active agent mixture. In one embodiment, the active agent mixture comprises solid hydrophobic active agent and pure or neat cationic delivery agent. In one embodiment, the solid hydrophobic active agent is crystalline. In another embodiment, the solid hydrophobic active agent is amorphous. In one embodiment, the method includes a step of crystallizing the hydrophobic active agent before it is combined with the cationic delivery agent. In another embodiment, the hydrophobic active agent is amorphous when it is combined with the cationic delivery agent. In one embodiment, the method includes a step of crystallizing the mixture of solid hydrophobic active agent and pure or neat delivery agent before combining the mixture with an aqueous carrier to form the delivery composition. In another embodiment, a mixture containing crystalline hydrophobic active agent and pure or neat delivery agent is combined with the aqueous carrier to form the delivery composition. In general, when solid hydrophobic active agent and solid hydrophobic cationic delivery agent are combined to form a mixture, the ratio of solid hydrophobic active agent:cationic delivery agent is less than about 1:5 to prevent the cationic delivery agent from solubilizing the hydrophobic active agent.

Kits and Articles of Manufacture

Another embodiment of the invention is directed towards kits and articles of manufacture. In particular, the present invention provides kits or packages including the delivery compositions described herein. In one embodiment, the invention provides a kit that includes one or more of the components of the delivery composition. As used herein "components of the delivery composition" can refer to one or more hydrophobic active agents, one or more cationic delivery agents, one or more pharmaceutically acceptable aqueous carriers, and any other additive, diluent, excipient, adjuvant, emulsifier, buffer, stabilizer, preservative included in the delivery composition. In one embodiment, the kit includes one or more hydrophobic active agents and one or more cationic delivery agent and instructions for combining the hydrophobic active agent and cationic delivery agent to form a delivery composition suitable for local administration. In one embodiment, the cationic delivery agent includes PEI. In another embodiment, the cationic delivery agent includes branched PEI. In a specific embodiment, the hydrophobic active agent is paclitaxel, sirolimus (rapamycin), everolimus, biolimus A9, zotarolimus, tacrolimus, and pimecrolimus and mixtures thereof.

In one embodiment, the kit includes at least about 1 mg/ml and up to about 25 mg/ml cationic delivery agent and at least about 5 mg/ml and up to about 125 mg/ml hydrophobic active agent, wherein the components are packaged individually, or combined, for example as a mixture of solids or as a liquid solution or suspension. In one embodiment, the kit includes at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml or 150 mg/ml hydrophobic active agent. In one embodiment, the kit includes at least about 0.1 mg/ml, 0.5 mg/ml, 1 mg/ml, 2 mg/ml, 3 mg/ml, 4 mg/ml, or 5 mg/ml and up to about 5 mg/ml, 10 mg/ml, 15 mg/ml, 20 mg/ml or 25 mg/ml cationic delivery agent. In one embodiment, the kit includes cationic delivery agent:hydrophobic active agent at a ratio of at least 1:25, for example, between about 1:1 and about 1:25, or at least about 1:2, 1:5 or 1:10 and up to about 1:10, 1:15, 1:20 or 1:25.

A number of packages or kits are known in the art for the use in dispensing pharmaceutical agents. The components of the delivery composition (for example, the hydrophobic active agent, the cationic delivery agent, the pharmaceutically acceptable aqueous carrier and/or any other additives) may be individually formulated or co-formulated and filled into suitable containers such as syringes, ampoules, or vials. It is envisioned that the aqueous carrier also may be provided in another container in the kit. The kits of the present invention also will typically include a means for containing the vials in close confinement for commercial sale such as, for example, injection or blow-molded plastic containers into which the desired vials are retained. In one embodiment, the kit includes an instrument for administration of the delivery composition, such as an inhalant, syringe, pipette, eye dropper, measuring spoon, or other such instrument, which can be used to apply the delivery composition to the desired tissue or organ of the patient.

In one embodiment, the kit provides one or more of the components of the delivery composition and instructions for combining the components for administration. In one embodiment, one or more of the components of the delivery composition in the kit is provided in dried or lyophilized forms. In one embodiment, the hydrophobic active agent, the cationic delivery agent, or both are provided as dried solids, individually or as a mixture. In another embodiment, the hydrophobic active agent, the cationic delivery agent, or both are provided as lyophilized solids, individually or as a mixture. In one embodiment, the hydrophobic active agent, the cationic delivery agent, or both are provided as amorphous solids, individually or as a mixture. In another embodiment, the hydrophobic active agent, the cationic delivery agent, or both are provided as crystalline solids, individually or as a mixture. When one or more components are provided as a dried solid, reconstitution generally is by the addition of a suitable aqueous carrier. In one embodiment, the aqueous carrier is water.

In another embodiment, one or more of the components of the delivery composition is provided as a solution or suspension. In one embodiment, the hydrophobic active agent, the cationic delivery agent, or both are provided as a solution or suspension, individually or as a mixture. For example, if individually provided, two solution components can be separated in a dual delivery syringe for ease of delivery to the site (for example dual delivery syringes and mini-dual delivery syringes available from Plas-Pak, Inc, Norwich, Conn.). In some instances, contents of a dual delivery syringe can be lyophilized to provide for a dual delivery syringe that contains a solution or suspension in one side and a dry powder in the other. Alternatively, the dual delivery syringe can contain lyophilized dry powder in both sides of the dual syringe. It is well known in the art that the lyophilized powder can be reconstituted at the point of use with physiologically acceptable fluid, such as phosphate buffered saline (PBS).

In one embodiment, one or more of the components of the delivery composition are provided as a dried solid in a container, individually or as a mixture, for example, as a crystallized solid or an amorphous solid, and are reconstituted with a pharmaceutically acceptable carrier prior to administration. In other embodiments, one or more of the components of the delivery composition are provided in as a liquid, in a container, individually or as a mixture, that may be administered with or without dilution. In one embodiment, one of the components of the delivery composition may be provided in solid form, which, prior to administration to a patient, is reconstituted with an aqueous liquid and another component of the delivery composition may be provided as a liquid solution or suspension, wherein the components are combined prior to administration. Each container may contain a unit dose of the active agent(s).

Methods of Use

The invention also provides a method for delivering a therapeutically effective amount of a hydrophobic active agent to a tissue, organ or organ system of a patient. In a more particular embodiment, the invention provides a method for local delivery of a therapeutically effective amount of a hydrophobic active agent to a solid tissue or organ of a patient. While not wishing to be bound by theory, it is believed that combining the hydrophobic active agent with a cationic delivery agent such as PEI improves adhesion of active agent to the tissue or organ surface, thereby increasing bioavailability and uptake of the hydrophobic active agent by tissue or organ to which it is applied. The cationic delivery agent may also disrupt some of the junctions between cells to increase permeability and allow the active agent to penetrate into the tissue or organ. It appears that the ability of the cationic delivery agent to improve therapeutic performance is most pronounced when used in combination with hydrophobic active agents. It is believed that more soluble hydrophilic active agents are more easily washed away from the surface of the tissue or organ by physiological fluids.

As used herein, the term "tissue" refers to an ensemble of similar cells from the same origin, that together carry out a specific function. Animal tissues can be grouped into four basic types: connective, muscle, nervous, and epithelial. Connective tissues are fibrous tissues made up of cells scattered throughout an extracellular matrix. Connective tissue helps maintain the shape of organs and helps holds them in place. Bone is an example of connective tissue. Muscle tissue functions to produce force and cause motion, either locomotion or movement within internal organs. Muscle tissue can be separated into three categories: visceral or smooth muscle, which is found in the inner linings of organs; skeletal muscle, in which is found attached to bone providing for gross movement; and cardiac muscle which is found in the heart. Nervous tissue functions to transmit messages in form of impulses. In the central nervous system, nervous tissue forms the brain and spinal cord. In the peripheral nervous system, nervous tissue forms the cranial nerves and spinal nerves. Epithelial tissue helps to protect organisms from microorganisms, injury, and fluid loss. The cells comprising an epithelial layer are linked via semi-permeable, tight junctions; hence, this tissue provides a barrier between the external environment and the organ it covers. In addition to this protective function, epithelial tissue may also be specialized to function in secretion and absorption. Epithelial tissues include cells that cover organ surfaces such as the surface of the skin, the airways, the reproductive tract, and the inner lining of the digestive tract.

As used herein, the term "organ" refers to a functional grouping of one or more tissues. Functionally related organs may cooperate to form organ systems. Examples of organs and organ systems found in mammals include, but are not limited to: the cardiovascular system, which includes organs such as the heart and blood vessels; the digestive system, which includes organs such as salivary glands, esophagus, stomach, liver, gallbladder, pancreas, intestines, colon, rectum and anus; the endocrine system, which includes endocrine glands such as the hypothalamus, pituitary gland, pineal body or pineal gland, thyroid, parathyroid and adrenal glands; the excretory system, which includes organs such as kidneys, ureters, bladder and urethra; the immune system, which includes tonsils, adenoids, thymus and spleen; the integumentary system, which includes skin, hair and nails; the muscular system, which includes voluntary and involuntary muscles; the nervous system, which includes brain, spinal cord and nerves; the reproductive system, which includes the sex organs, such as ovaries, fallopian tubes, uterus, vagina, mammary glands, testes, vas deferens, seminal vesicles, prostate and penis; the respiratory system, which includes the pharynx, larynx, trachea, bronchi, lungs and diaphragm; and the skeletal system, which includes bones, cartilage, ligaments and tendons. As used herein, the terms "tissue" and "organs" refer to solid tissues or organs, rather than blood or other biological liquids such as spinal fluid, amniotic fluid or peritoneal fluid.

As used herein, an "individual" or a "patient" is a vertebrate, for example, a mammal. The term "mammal" can also refer to any animal classified as a mammal, including humans, domestic and farm animals, and zoo, sports, or pet animals, such as dogs, horses, cats, cows, etc. In a more particular embodiment, the mammal is human.

The term "effective amount" refers to an amount effective, at dosages and for periods of time necessary, to achieve the desired therapeutic or prophylactic result. A "therapeutically effective amount" of the delivery composition of the invention may vary according to factors such as the disease state, age, sex, and weight of the individual, and the ability of the substance/molecule, agonist or antagonist to elicit a desired response in the individual. A therapeutically effective amount is also one in which any toxic or detrimental effects of the composition are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount may be less than the therapeutically effective amount.

In one embodiment, the invention provides a method for treating a tissue or organ of a patient. As used herein, the terms "treat", "treating" and "treatment" refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, decreasing the rate of disease progression, amelioration or palliation of the disease state, and remission or improved prognosis. As used herein, the terms "prevent", "preventing" and "prevention" refer to a method for preventing an organism from acquiring a disorder.

The delivery composition may be a topical, syringable, or injectable formulation; and is suitable for local delivery of the active agent. For topical administration, the delivery composition is applied directly where its action is desired. Methods for topical delivery include the use of ointments, creams, emulsions, solutions, suspensions and the like. In other embodiments, the delivery composition is administered by application through a cannula, by injection, or as part of a lavage. Compositions for these types of local delivery can include solutions, suspensions and emulsions.

Examples of local administration include, but are not limited to, epicutaneous administration (i.e., application onto the skin); inhalation, for example, with asthma medications; as an enema for local administration to the bowel; ocular, for example, as eye drops for local administration to the conjunctiva; aural, for example, as ear drops; or intranasal. In other embodiments, an active agent can be administered locally from a device such as a balloon catheter. In another embodiment, local administration includes the lavage of an open wound, the lavage containing delivery compositions described herein with antimicrobials or other wound healing medicaments. In a more particular embodiment, local administration includes oral lavage, for example, a mouthwash.

In some embodiments, the delivery composition can be administered using a balloon catheter. The delivery composition can be infused through a lumen or lumens of a balloon catheter to administer the composition to the desired site where the drug effect is warranted. For example, the site can be a segment of an artery, vein or neurovascular. The method allows for isolation and subsequent perfusion of the target organ (e.g. for tumor treatment). One specific embodiment of administration can be the use of a dual occlusion balloon (e.g. TAPAS balloon system available from Spectranectics International, BV, Leusden, The Netherlands) for precise targeting of a treatment area (e.g. intra-arterially). Use of delivery compositions as disclosed herein can increase targeting of the treatment area with the drug being delivered, thus further minimizing unwanted systemic effects of the drug. Other balloon catheter methods of use include balloon sinuplasty (e.g. Reneva® and Relieva Ultirra™; available from Acclarent, Menlo Park, Calif.)

In yet other embodiments, a medical device such as a balloon catheter can be coated with the delivery composition described herein. In one embodiment, the balloon catheter can be coated in a collapsed state. In another embodiment, the balloon catheter can be coated in a partially or fully expanded state. In one embodiment, the balloon catheter can be coated with the coating materials described herein and a bioactive material such as a chemical ablative (e.g. vincristine, paclitaxel) and further used for renal artery denervation therapy for hypertension.

Delivery compositions of the present disclosure can also be used in conjunction with microinfusion catheters. Such catheters can be used to deliver drug, for example, for renal denervation for direct infusion into the vessel wall (Bullfrog® and Cricket microinfusion catheters available from Mercator MedSystems, Inc.,). Microinfusion catheters with delivery compositions of the present disclosure can also be used to form an embolic block, such as in neurovascular applications or treatment of the vascular supply of tumors. Other neurovascular methods of use include, but are not limited to, brachytherapy treatment for brain cancer applications (GliaSite Radiation Therapy System available from IsoRay, Medical, Richland, Wash.).

Delivery compositions described herein can also be used in connection with treating stenosis such as bladder neck stenosis (BNS), a complication associated with transurethral resection of the prostate; laryngotracheal stenosis, for example, in conjunction with serial endoscopic dilation to treat subglottic stenosis; and bile duct stenosis, for example, subsequent to pancreatic, hepatocellular or bile duct cancer.

Delivery compositions described herein can be combined with treatments that use RF-susceptible microparticles to improve uptake of the microparticles in the tissue at the site of the tumor or other targeted organ. Other embodiments for topical administration include, but are not limited to, oral cavity delivery of chemotherapeutics, for example with mouthwashes. Additionally, studies have shown that delivery of rapamycin to the oral cavity can prevent radiation-induced mucositis and that it can be desirable to reduce the systemic levels of rapamycin to avoid toxicities associated with the drug (*Cell Stem Cell*, Sep. 7, 2012, Vol. 11:3, pp. 287-288).

Delivery compositions described herein can be used to increase drug-uptake in the lung. One embodiment envisioned to be used for delivery compositions for inhalation therapy can be a metered-dose inhaler (available from 3M Company, St. Paul, Minn.). Compositions described herein can increase drug uptake in the lung to provide for improved speed of drug effect, an important aspect when treating disease states such as asthma.

Other methods of use include treatment of joint disorders (e.g. arthritis). Local injections of drug (e.g. cortisone) are desirable to be kept at the site of the affected joint for extended term.

Some embodiments of the method of use include localized treatment of the lining of the esophagus. Barrett's esophagus (pre-cancer esophagus lining) after BARRX treatment (ablation) requires delivery of local healing agents to the affected site for improved outcomes. Delivery compositions disclosed herein can increase uptake of healing agents by the treated esophagus.

Other exemplary methods of use for the local delivery compositions described herein include direct injections into a cancerous tumor, intraperitoneal tumor treatment, and sclerotherapy. Additionally, percutaneous delivery systems of biologics for the treatment of cardiovascular disease can use the delivery composition of the present disclosure. Treatments such as those under the trade name JVS-100, promotes tissue repair through recruitment of endogenous stem cells to the damaged organ (available from BioCardia, Inc, San Carlos, Calif.). These devices allow delivery into the heart using the Helical Infusion Catheter for transendocardial intramyocardial injection of therapies (also from BioCardia).

EXAMPLES

As used in the Examples, the term "jar-Milled Paclitaxel" refers to Paclitaxel (LC laboratories) that was suspended in water at 65 mg/mL and milled using 5 mm stabilized zirconia 5×5 mm cylindrical beads (Stanford Materials Corp). After milling for 18 hours the slurry was removed from the beads and lyophilized. The term "sonicated Paclitaxel" refers to Paclitaxel crystals that were obtained by suspending paclitaxel (LC Laboratories) in water at 50 mg/mL. The paclitaxel was micronized using a sonic probe for 30 seconds, and leaving the resulting suspension for three days at room temperature on an orbital shaker with a 1 hour sonication treatment per day in a sonic bath over the course of the three days. The mixture was lyophilized.

Example 1

Polyethylenimine (PEI) Mediated Transfer of Paclitaxel (PTX) to Surfaces

Delivery of paclitaxel to surfaces with or without seeded endothelial cells was studied in-vitro using untreated 24-well polystyrene tissue culture plates (TCPS); Matrigel™ coated 24-well cell culture plates (BD Matrigel™ Matrix Thin-Layer cell; available from Becton Dickinson Biosciences, Franklin Lakes, N.J.), or 24-well cell culture plates treated with heparin-containing HP01 coating or collagen containing CL01 coating (available from SurModics, Eden Prarie, Minn.). Human coronary endothelial cells (HCAECs, available Lonza, Walkersville, Md.) were cultured in EGM™-2MV growth media (available from Lonza, Walkersville, Md.). One day prior to paclitaxel transfer studies, cells were seed in the various culture plates at 50,000 cells per well in 0.5 mL of medium. Suspensions of paclitaxel (available from LC Laboratories, Woburn, Mass.) in water were prepared at 55.2 mg/ml paclitaxel with or without PEI (available from Polysciences, Warrington, Pa., MW=750 kDa) at 4.8 mg/ml. The suspensions were sonicated briefly. Resulting suspensions (6.7 µL) were added to cell media (100 µL) and put in the cell culture plates and incubated for 3 minutes. Suspensions were also added to the different 24-well plates with 100 µL medium (100 µL) but without seeded cells. After incubation plates were rinsed three times with phosphate buffered saline (500 µL per well) and then allowed to dry overnight. Paclitaxel remaining in plates as a result of adhesion was dissolved in 250 µL methanol and quantified by HPLC. The amount of transferred paclitaxel is shown in FIG. 1.

Example 2

Delivery of Paclitaxel to Surfaces with or without Seeded Endothelial Cells

Figure 2:
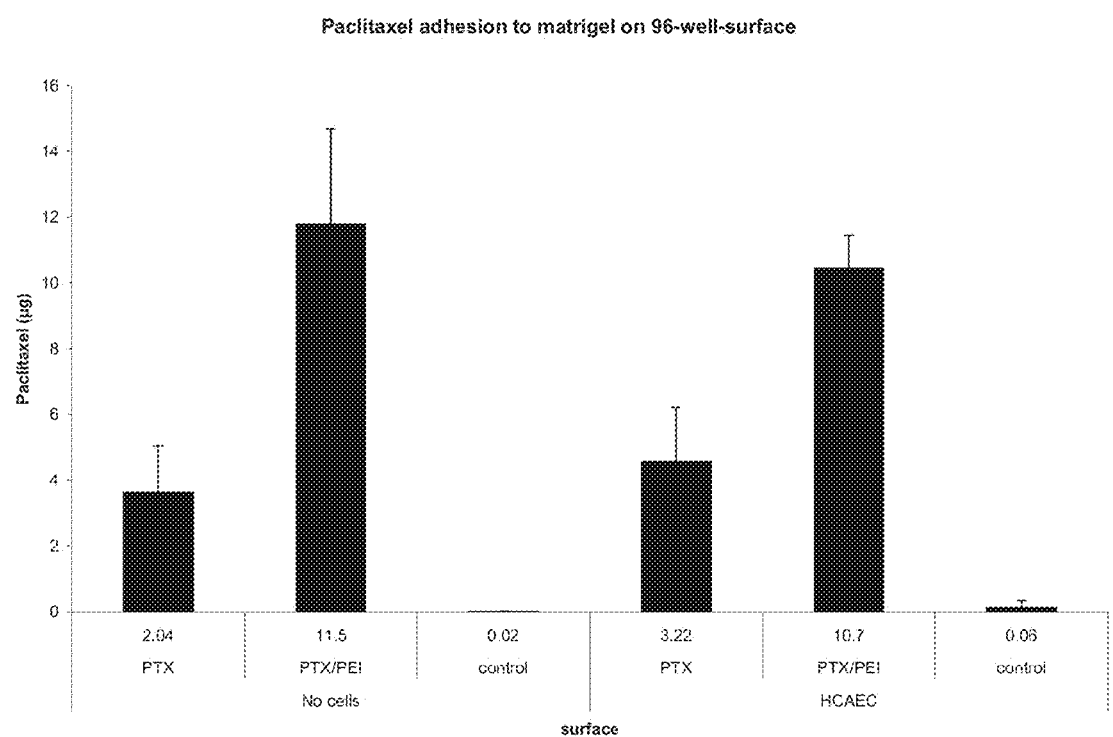
FIG. 2 is a graph showing the amount of paclitaxel transferred to Matrigel™ surfaces with or without seeded endothelial cells in the presence or absence of PEI.

Delivery of paclitaxel to surfaces with or without seeded endothelial cells was studied in-vitro using Matrigel™ coated 96-well cell culture plates (BD Matrigel™ Matrix Thin-Layer cell, available from Becton Dickinson Biosciences, Franklin Lakes, N.J.). Human coronary endothelial cells (HCAECs, available from Lonza, Walkersville, Md.) were cultured in EGM™-2MV growth media (available from Lonza, Walkersville, Md.). One day prior to paclitaxel transfer studies, cells were seed in the various culture plates at 20,000 cells per well in 0.2 mL of medium. Suspensions of paclitaxel (LC Laboratories, Woburn, Mass.) in water were prepared at 11 mg/ml paclitaxel with or without PEI (available from Polysciences, Warrington, Pa.; MW=750 kDa) at 1 mg/ml. Suspensions were sonicated briefly prior to use. Resulting suspensions (5 µL) were added to 0.1 mL of cell media and put in the cell culture plates and incubated for 3 minutes. Suspensions were also added to the Matrigel™ coated plate with 0.1 mL medium but without seeded cells. After incubation plates were rinsed three times with phosphate buffered saline (0.2 mL per well) and then allowed to dry overnight. Paclitaxel remaining in plates as a result of adhesion was dissolved in 250 µL methanol/0.1% acetic acid and quantified by HPLC. The amount of transferred paclitaxel is shown in FIG. 2.

Example 3

Figure 3:
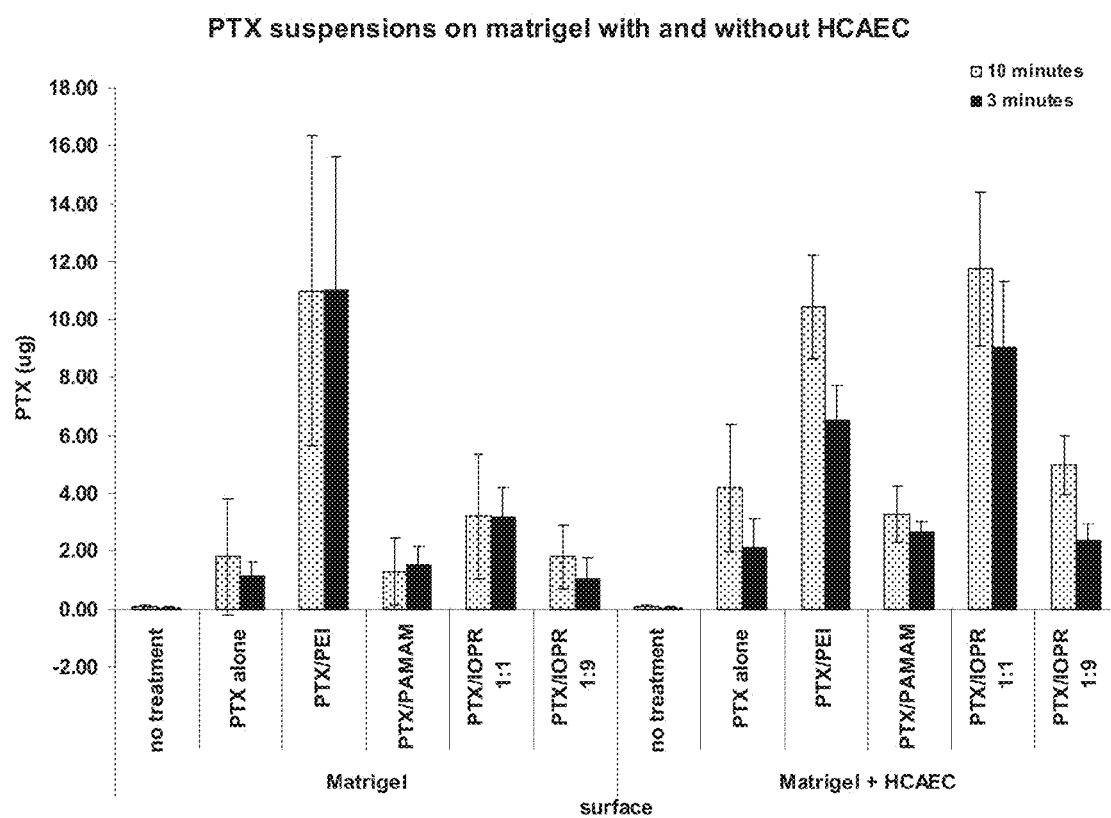
FIG. 3 is a graph showing delivery of paclitaxel to endothelial cells and tissues using cells grown on Matrigel™ coated cell culture plates in the presence or absence of PEI and other excipients such as radio-opaque iopromide.

Polyethyleneimine (PEI) Mediated Transfer of Paclitaxel (PTX) to Endothelial Cell Surface or Extracellular Matrix Surfaces Delivery of paclitaxel to endothelial cells and tissue was studied in vitro using cells grown on Matrigel™ coated cell culture plates. Human coronary endothelial cells (HCAECs, Lonza, Walkersville, Md.) were cultured in EGM™-2MV growth media (Lonza, Walkersville, Md.). One day prior to paclitaxel transfer studies, cells were seed in 96 well BD Matrigel™ Matrix Thin-Layer cell culture plates at 20,000 cells per well in 0.2 mL of medium. Suspensions of paclitaxel (LC Laboratories, Woburn, Mass.) in water were prepared at 11 mg/ml paclitaxel and with PEI (Polysciences, Warrington, Pa.; MW=750 kDa) or PAMAM, ethylene diamine core, gen 4, dendrimer (Sigma, Milwaukee, Wis.; 14,214 Da) at 0.96 mg/mL (92:8 w/w ratio) or iopromide at 11 mg/mL (IOPR, 1:1 w/w ratio). Suspensions were sonicated briefly prior to use. Resulting suspensions (5 µL) were added to the cell culture plates and incubated for 3 or 10 minutes. Suspensions were also added to Matrigeff coated plates with medium but without cells. After incubation plates were rinsed three times with phosphate buffered saline (200 µL per well) and then allowed to dry overnight. Paclitaxel remaining in plates was dissolved in methanol (250 µL) and quantified by HPLC. The amount of transferred paclitaxel is shown in FIG. 3.

Example 4

Adhesion of Paclitaxel to Surfaces in the Presence of Heparin

Figure 4:
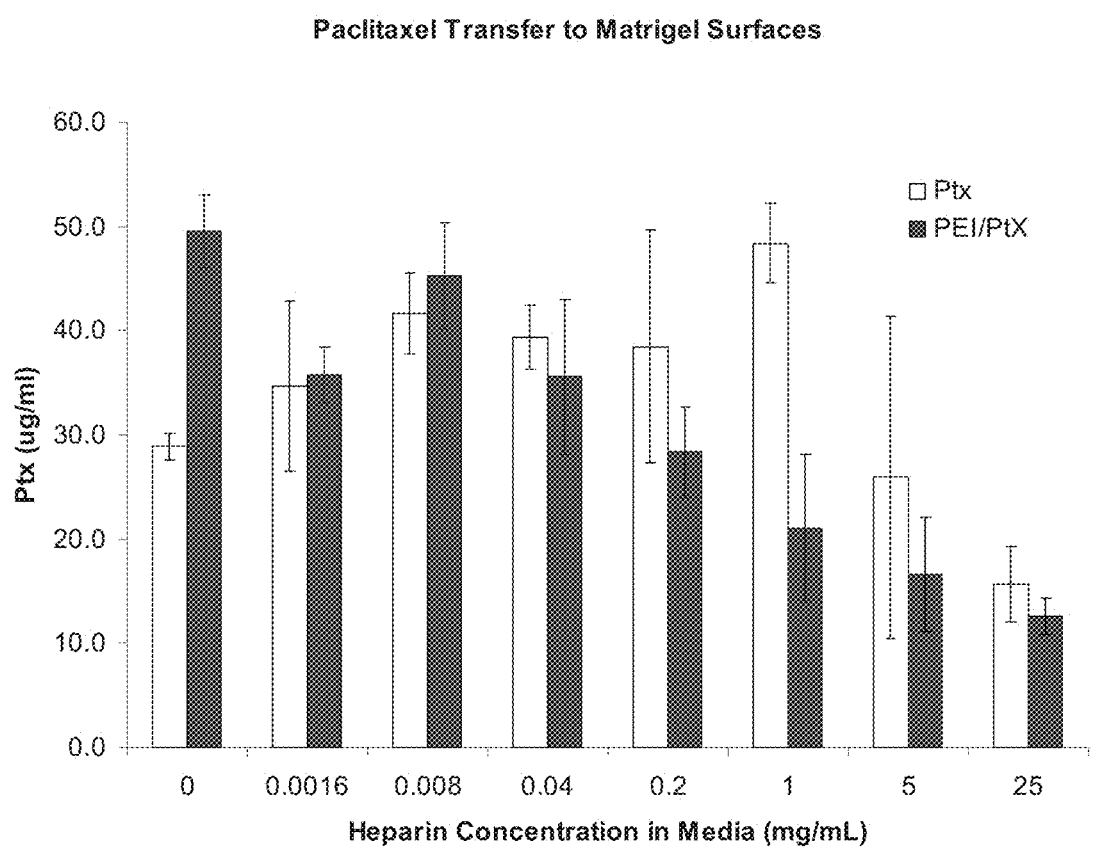
FIG. 4 is a graph showing the amount of paclitaxel transferred to Matrigel™ surfaces in the presence of varying concentrations of heparin in the presence or absence of PEI.
Figure 5:
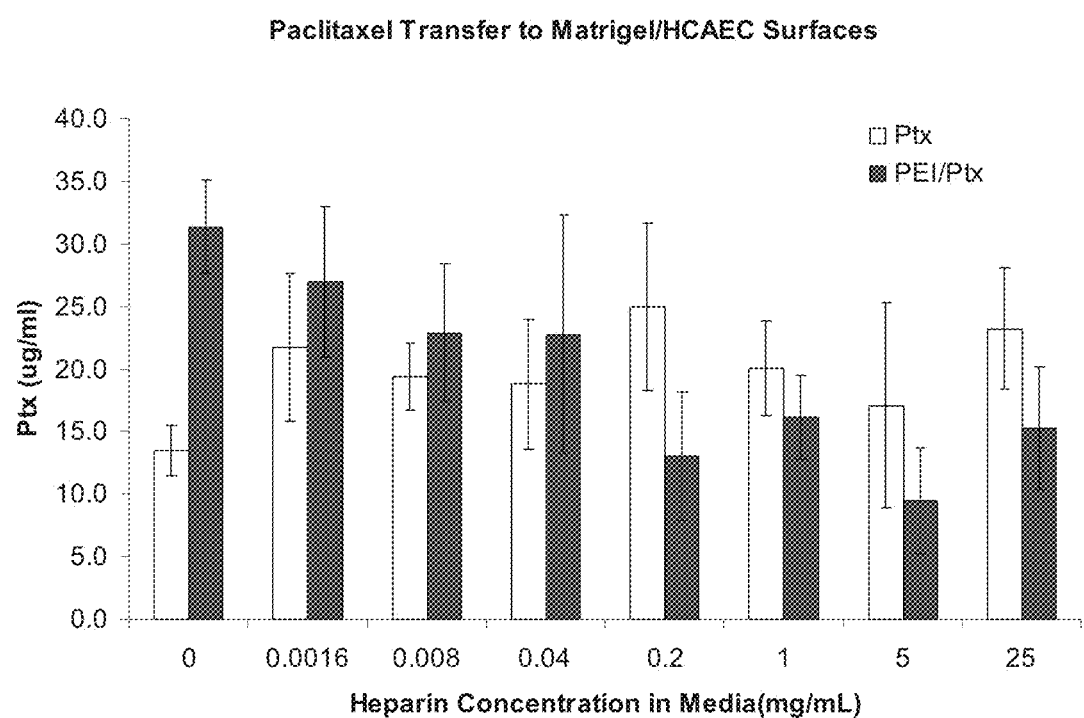
FIG. 5 is a graph showing the amount of paclitaxel transferred to Matrigel™/HCAEC surfaces in the presence of varying concentrations of heparin in the presence or absence of PEI.

Adhesion of paclitaxel to surfaces in the presence of heparin at varied concentrations with or without seeded endothelial cells was studied in-vitro using Matrigel™ coated 96-well cell culture plates (BD Matrigel™ Matrix Thin-Layer cell, BD Biosciences, San Jose, Calif.). Human coronary endothelial cells (HCAECs, Lonza, Walkersville, Md.) were cultured in EGM™-2MV growth media (Lonza, Walkersville, Md.). One day prior to paclitaxel transfer studies, cells were seed in the various culture plates at 20,000 cells per well in 0.2 mL of medium. Prior to adding paclitaxel, heparin (Sodium Salt, Celsus, Cincinnati, Ohio) was dissolved in growth medium at concentrations of 25, 5, 1, 0.2, 0.04, 0.008 and 0.0016 mg/ml and media in cell culture plates was replaced with heparin containing medium. Suspensions of paclitaxel (LC Laboratories, Woburn, Mass.) in water were prepared at 11 mg/ml paclitaxel with or without PEI (Polysciences, Warrington, Pa.) at 1 mg/ml. Suspensions were sonicated briefly prior to use. 5 µL of suspensions were added to the growth media in plates with and without cells and incubated for 4 minutes. After incubation plates were rinsed three times with phosphate buffered saline (0.2 mL per well) and then allowed to dry overnight. Paclitaxel remaining in plates as a result of adhesion was dissolved in methanol (60 µL) and quantified by HPLC. The amount of transferred paclitaxel with and without PEI and varying heparin concentrations is shown in FIGS. 4 and 5.

Example 5

Adhesion of Paclitaxel to Surfaces with or without Seeded Endothelial Cells

Figure 6:
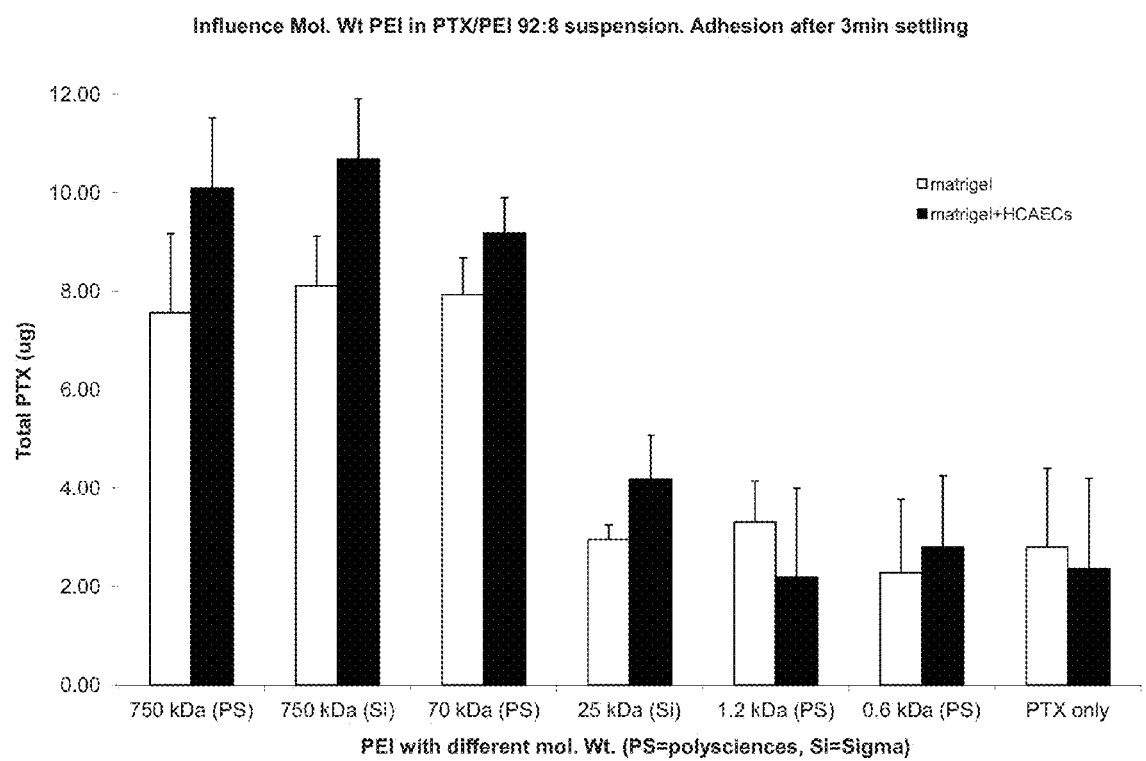
FIG. 6 is a graph showing the influence of molecular weight in adhesion of paclitaxel to surfaces with or without seeded endothelial cells.

Adhesion of paclitaxel to surfaces with or without seeded endothelial cells was studied in-vitro using Matrigel™ coated 96-well cell culture plates (BD Matrigel™ Matrix Thin-Layer cell). Human coronary endothelial cells (HCAECs, Lonza, Walkersville, Md.) were cultured in EGM™-2MV growth media (Lonza). One day prior to Paclitaxel transfer studies, cells were seeded in wells of column 7 to 12 of the culture plate at 20,000 cells per well in 0.2 mL of medium. After 24 hours incubation the medium was replaced with 100 ul fresh medium in all wells. Suspensions of Paclitaxel (LC Labs, 'sonicated') in aqueous branched PEI solutions were prepared at 11 mg/ml paclitaxel and PEI at 1 mg/ml. Branched PEI of different molecular weights were used: 750 kDa from both polysciences and Sigma, 70 kDa and 25 kDa from Sigma, 1200 Da and 600 Da from polysciences. All suspensions were sonicated briefly prior to use to ensure that all components were well distributed. In 12 wells per formulation (6 with and 6 without HCAEC seeded on top of the matrigel): 5 µL of the suspension was added to 0.1 mL of cell media. The plate was incubated for 3 minutes during which time the suspension was allowed to settle. After incubation the plate was rinsed three times with phosphate buffered saline (0.2 mL per well) and then allowed to dry overnight. Paclitaxel remaining in the plate as a result of adhesion was dissolved in 250 µL methanol/0.1% acetic acid and quantified by HPLC. The amount of transferred paclitaxel is shown in FIG. 6.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

In the Specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

All publications and patent applications in this specification are indicative of the level of ordinary skill in the art to which this invention pertains. All publications and patent applications are herein incorporated by reference to the same extent as if each individual publication or patent application was specifically and individually indicated by reference. To the extent inconsistencies arise between publications and patent applications incorporated by reference and the present disclosure, information in the present disclosure will govern.

The invention has been described with reference to various specific and preferred embodiments and techniques. However, it should be understood that many variations and modifications may be made while remaining within the spirit and scope of the invention.

What is claimed is:

1. A delivery composition for local administration of a hydrophobic active agent, the delivery composition comprising:
    a cationic delivery agent comprising an agent selected from the group consisting of 1,2-dioleoyl-3-trimethylammonium-propane (DOTAP), polyamidoamine dendrimers (PAMAM), polypropylenimine, and polyethyleneimine (PEI) homopolymer;
    the hydrophobic active agent, wherein the hydrophobic active agent interfaces with the cationic delivery agent; and
    a pharmaceutically acceptable aqueous carrier;
    the cationic delivery agent effective to improve adhesion of the hydrophobic active agent to surfaces;
    wherein the delivery composition is in the form of a liquid immediately prior to local administration.

2. The composition according to claim 1, wherein the cationic delivery agent comprises branched PEI.

3. The composition according to claim 2, wherein the branched PEI has a molecular weight of at least about 25 kD and up to about 5000 kD.

4. The composition according to claim 2, wherein the branched PEI has a molecular weight of at least about 100 kD and up to about 3000 kD.

5. The composition according to claim 2, wherein branched PEI has a ratio of primary:secondary:tertiary amines between about 1:3:1 and about 1:1:1.

6. The composition according to claim 2, wherein branched PEI has a ratio of primary:secondary:tertiary amines of between about 1:2:1 and about 1:1:1.

7. The composition according to claim 1, comprising cationic delivery agent:hydrophobic active agent at a ratio of at least about 1:1 and up to about 1:25.

8. The composition according to claim 1, comprising cationic delivery agent:hydrophobic active agent at a ratio of at least about 1:2 and up to about 1:20.

9. The composition according to claim 1, comprising cationic delivery agent:hydrophobic active agent at a ratio of at least about 1:5 and up to about 1:10.

10. The composition according to claim 1, comprising at least about 1 mg/ml and up to about 25 mg/ml cationic delivery agent.

11. The composition according to claim 1, comprising at least about 5 mg/ml and up to about 125 mg/ml hydrophobic active agent.

12. The composition according to claim 1, wherein the aqueous carrier is selected from water and buffered saline.

13. The composition according to claim 1, comprising a pH between 5 and 9.

14. The composition according to claim 1, wherein the hydrophobic active agent is selected from an antiproliferative, analgesic, anti-inflammatory, anti-arrhythmic, anti-bacterial, anti-coagulant, anti-hypertensive, anti-muscarinic, anti-neoplastic, beta-blocker, cardiac inotropic agent, corticosteroids, lipid regulating agents, anti-anginal agents, and combinations thereof.

15. The composition according to claim 1, wherein the hydrophobic active agent comprises an antiproliferative selected from paclitaxel, sirolimus, everolimus, biolimus A9, zotarolimus, tacrolimus, and pimecrolimus and mixtures thereof.

16. A method for local administration of a hydrophobic active agent to a tissue or organ of a patient, the method comprising:
    preparing a composition comprising
        a cationic delivery agent comprising an agent selected from the group consisting of 1,2-dioleoyl-3-trimethylammonium-propane (DOTAP), polyamidoamine dendrimers (PAMAM), polypropylenimine, and polyethyleneimine (PEI) homopolymer;
        the hydrophobic active agent, wherein the hydrophobic active agent interfaces with the cationic delivery agent; and
        a pharmaceutically acceptable aqueous carrier, the cationic delivery agent effective to improve adhesion of the hydrophobic active agent to surfaces; and
    applying the composition to the tissue or organ of the patient, wherein the composition is in a liquid form as applied.

17. The method of claim 16, wherein the PEI has a molecular weight of at least about 25 kD and up to about 5000 kD.

* * * * *